Figure 1:
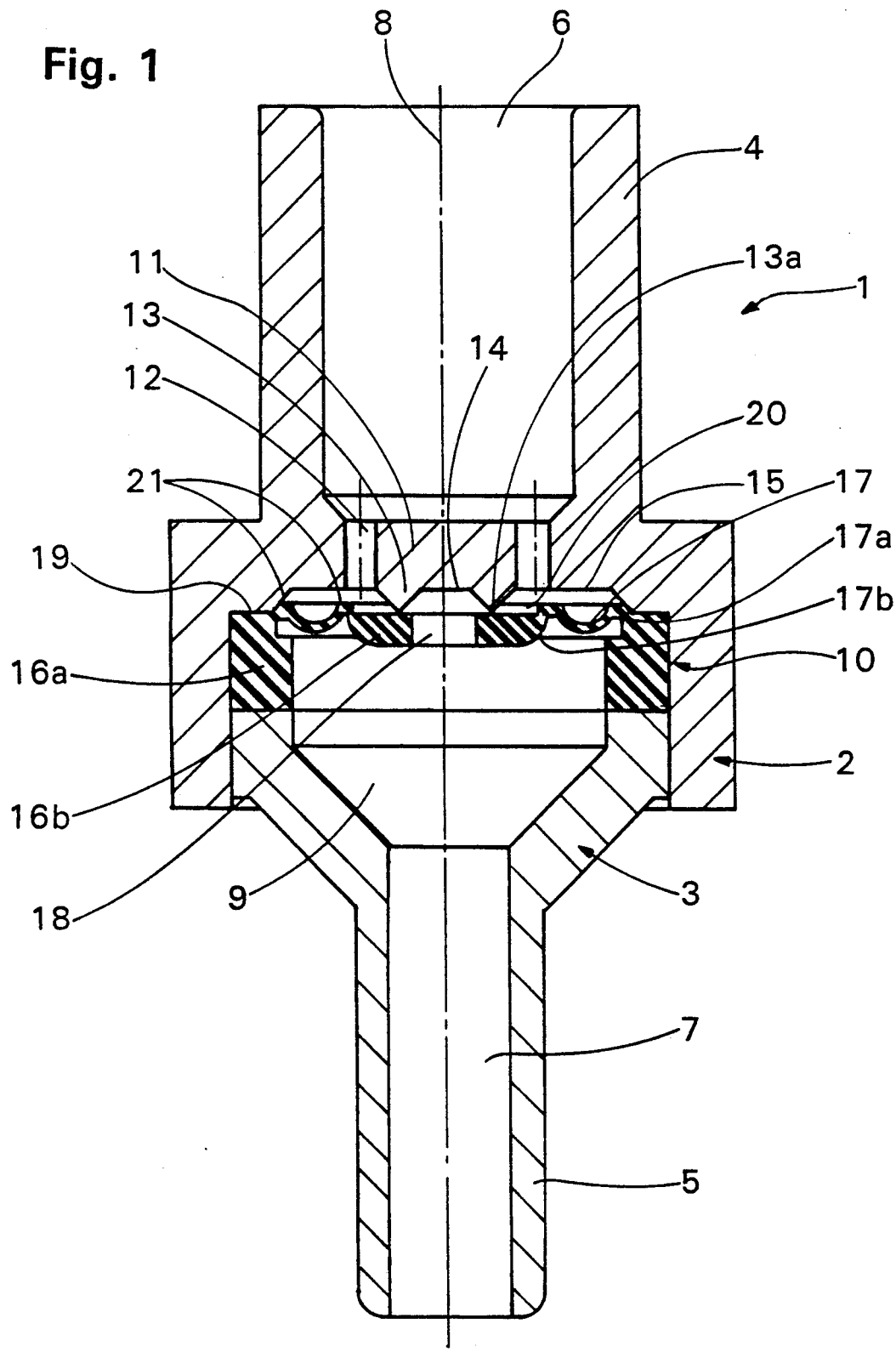

United States Patent [19]

Forberg

[11] Patent Number: 5,305,795
[45] Date of Patent: Apr. 26, 1994

[54] NONRETURN VALVE, IN PARTICULAR FOR MEDICAL INFUSION APPLIANCES

[76] Inventor: Hans-Jürgen Forberg, Sebenter Weg 4, D-2432 Damlos, Fed. Rep. of Germany

[21] Appl. No.: 916,837
[22] PCT Filed: Nov. 16, 1991
[86] PCT No.: PCT/DE91/00896
§ 371 Date: Aug. 7, 1992
§ 102(e) Date: Aug. 7, 1992
[87] PCT Pub. No.: WO92/10232
PCT Pub. Date: Jun. 25, 1992

[30] Foreign Application Priority Data

Dec. 13, 1990 [DE] Fed. Rep. of Germany ....... 4039814

[51] Int. Cl.$^5$ .............................................. F16K 15/14
[52] U.S. Cl. ................................................ 137/859
[58] Field of Search ............................... 137/496, 859

[56] References Cited

U.S. PATENT DOCUMENTS

| | | |
|---|---|---|
| 3,270,771 | 9/1966 | Morgan ................. 137/859 |
| 3,354,902 | 11/1967 | Obermair ............... 137/859 X |
| 3,827,456 | 8/1974 | Sheppard .............. 137/859 |
| 4,593,720 | 6/1986 | Bergandy ............... 137/859 |
| 4,776,839 | 10/1988 | Doumenis ............ 137/859 X |

FOREIGN PATENT DOCUMENTS

| | | |
|---|---|---|
| 0333305 | 9/1989 | European Pat. Off. . |
| 806301 | 6/1951 | Fed. Rep. of Germany ...... 137/859 |
| 2603712 | 8/1977 | Fed. Rep. of Germany ...... 137/859 |
| 8805638 | 7/1988 | Fed. Rep. of Germany . |
| 2142846 | 2/1973 | France . |

*Primary Examiner*—Robert G. Nilson
*Attorney, Agent, or Firm*—Panitch Schwarze Jacobs & Nadel

[57] ABSTRACT

A nonreturn valve has a housing (1) provided with a central chamber (9) into which open an inlet channel (6) and an outlet channel (7) that may be separated by a sealing membrane (10) provided with a flow passage (18). The membrane (10) has a marginal part (16a) clamped in the housing (1), a central sealing part (16b) and a thinner annular wall (17) that links both parts (16a,16b). In order to obtain a nonreturn valve that has a reliable operation even at the smallest differential pressures, a central crater-like sealing formation (13,14), for example, is provided in the membrane (10). The inflow from the inlet channel (6) to the membrane (10) takes place outside the crater-like sealing structure (13,14) and the flow passage (18) of the membrane (10) is located within the crater-like sealing structure (13,14). The thinner annular wall (17) of the membrane (10), that generates a sealing pre-stress, has a shaped cross-section and its open junctures (17a,17b) adjacent to the marginal part and to the central sealing part (16b) of the membrane (10) are located at least approximately in the same plane, that coincides with the sealing plane, or is parallel thereto.

12 Claims, 1 Drawing Sheet

U.S. Patent    Apr. 26, 1994    5,305,795

NONRETURN VALVE, IN PARTICULAR FOR MEDICAL INFUSION APPLIANCES

The invention relates to a nonreturn valve, in particular for use in connection with medical infusion appliances, comprising a housing with a central chamber into which open an inlet channel and an outlet channel, which channels may be separated by a sealing membrane provided with a flow passage, wherein the membrane has a marginal part clamped in the housing, a central sealing part and a thinner annular wall that links both parts.

Such a nonreturn valve is described in the EP-A-02 47 824. This valve is not suited for slight pressure differences between its inflow side and its outflow side, i.e. the valve does not ensure a reliable opening and closing when the pressure differences are slight. In order to operate at all with small pressure differences, the initial tension of the clamped-in membrane in this valve must only be very small. However, this condition can be maintained only with great difficulty and especially because of the tight manufacturing tolerances that have to be adhered to in the manufacture of these valves, even small deviations lead to relatively large drawbacks. However, small manufacturing tolerances result in higher manufacturing costs. Also the opening force for the membrane is relatively high, which inter alia can be traced back to the construction and the shape and the clamping position of the membrane.

Nonreturn valves such as these are used in medical technology, e.g. in the so-called parallel infusion technique in which, for example by means of an infusion pump or a syringe, medicines in very small quantities are added via a secondary connection to an infusion solution which is administered to a patient through an infusion bottle by drip feeding. Care must be taken in this case to prevent the medicine from the infusion pump to flow back into the drip-feed, which danger exists when the flow of the infusion solution to the patient is inadvertently blocked, perhaps temporarily. The nonreturn valves in question for this reason are so constructed that during the normal operation they link the two systems together in the inflow direction to the patient, but separate them in the opposite direction.

The demands made on a nonreturn valve of this type are therefore very high. It must be ensured for example that the nonreturn valve opens at a pressure of as low as 0.01 bar, which is produced by gravity, in order to allow the unrestricted inflow of infusion solution, and on the other hand it has to withstand a closure pressure of approximately 6 bar which can occur during a fault in the pump system. The said opening sensitivity must also be present immediately after the effect of the full closure pressure. It must also be able to reliably shut down conveying rates of 0.1 ml/h, as this is normally the lowest conveying rate used in the injection pumps.

A further nonreturn valve proposed for the application mentioned is the subject of EP-A-01 82 045 which shows such a nonreturn valve with a sealing disc which in the rest position is held against the inlet opening by a central two-point support and which through the infusion pressure of the gravity system is displaced in a bow-like manner, so that the infusion solution can flow around the sealing disc. A similar solution is described in the DE-U-87 17 726. Finally in the DE-C-26 05 348 is shown a nonreturn valve which operates by a valve disc floating upwards when there is an overpressure in the pump system.

Tests have shown that, in common with all the said nonreturn valves, at least one of the said requirements cannot be met by them. Test results are published in an article of the journal "Biomedizinische Technik", volume 35, issue No. 3/1990, which article raises further requirements to be addressed to such nonreturn valves. Of special emphasis in this case is the throughflow preventing flow resistance caused by the nonreturn valve which leads to a reduction in the throughflow which, for the purpose of precisely controlling the throughflow, should be kept as low as possible.

The object of the invention therefore is to improve a nonreturn valve of the type mentioned at the beginning so as to optimally meet the said requirements and which ensures a reliable opening and closing even when there are only slight pressure differences and especially in a simple construction which is largely independent of manufacturing tolerances.

The solution to this object is disclosed in patent claim 1.

Preferred embodiments of the nonreturn valve according to the invention are described in the sub-claims.

This solution ensures a safe operation of the nonreturn valve with small difference in pressure, and especially when there are unacceptable measurement deviations as a result of excessive manufacturing tolerances in the parts of the valve which are operationally important. This is attributable to the fact that the opening pressure from the inlet channel acts on an area of the membrane outside the sealing crater, so that with a small pressure difference a large opening force is achieved through a large surface of the membrane. The pretension of the membrane can therefore be large and an improved sealing reliability of the valve is therefore achieved. The valve can also be manufactured with greater manufacturing tolerances without losing any of its required effectiveness. Its construction also remains simple.

An embodiment example of the invention is now described in more detail with the aid of the drawing which through its single diagram shows a longitudinal section of a nonreturn valve according to the invention.

According to this, the nonreturn valve consists of a housing 1 which is composed of a first and second housing 2 or 3. The two housing parts 2 and 3 are preferably constructed by injection moulding a suitable thermoplastic and each have a tubular piece 4 or 5 surrounding an inlet channel 6 or outlet channel 7, the channels being aligned relative to each other, i.e. arranged on a common axis 8. The two housing parts 2 and 3 are connected to each other and delimit a central chamber 9 of essentially cylindrical shape in which a membrane 10 of highly flexible material is sealingly clamped in its marginal region between the housing parts 2 and 3.

The chamber 9 is limited for example by a diagonal wall 11, provided in the inlet channel 6 on the outflow side, which in its marginal region is provided with small through drillings 12, which are arranged on a circular line concentrically running about the axis 8, and which connect the inlet channel 6 to the chamber 9. The diagonal wall 11 has a central crater-like sealing structure 13, 14 which is provided within the circle for the drillings 12. The crater-like sealing ring 13 projects from the diagonal wall 11 in the direction of the membrane 10, thereby producing a recessed inner crater surface 14, and a recessed outer annular surface 15. The drillings 12 of the diagonal wall 11 flow into the recessed annular surface 15. Also provided is an annular clamping surface 19 for the outer marginal area of the membrane 10 which is situated preferably substantially in the same plane with the sealing surface 20 of the membrane or with the sealing edge 13a of the crater-like sealing ring 13.

The membrane 10 has a clamped, thicker marginal part 16a and is furthermore provided with a disc-shaped central sealing part 16b which latter cooperates with the crater-like sealing ring 13 for achieving a seal which can be opened up. A preferably bead-shaped, profiled thinner annular wall 17 is connected both to the clamped annular part as well as also to the sealing part of the membrane 10. The diameter of the sealing part 16b is therefore slightly larger than the diameter of the perforated circle for the drillings 12. The sealing part 16b finally has a small flow passage 18 which connects the space situated inside the crater-like sealing formation 13 with the remaining chamber 9 from which flows the outlet channel 7. The cross-section of the annular wall 17 for example is curved in such a way that the apex of the curve points away from the diagonal wall 11. However, when under stress the annular wall 17 can be pushed through to such an extent that it comes to rest against the annular surface 15 which, through further flexing, relieves the stress. The annular wall 17 is furthermore so arranged that its junctures 17a, 17b in the marginal part 16a or in the central sealing part 16b of the membrane 10 are arranged at least approximately in a common plane that again coincides with the sealing surface 20 of the membrane.

In an alternative embodiment the crater-like sealing structure 13 can also be provided on the central sealing part 16b of the membrane 10, so that the sealing surface 20 is then formed on the diagonal wall 11. The thin annular wall 17 can also have a triangular or rectangular cross-section, preferably however so that it has a symmetrical wall profile.

In a further variation the sealing surface 20 of the membrane 10 (or alternatively the diagonal wall 11) can also run parallel to the common plane of the junctures 17a, 17b of the annular wall 17, instead of coinciding with it. As the drawing shows, the clamping surface 19 of the marginal part 16a of the membrane 10 can additionally coincide at least approximately with the common plane of the junctures 17a, 17b and with the sealing surface 20.

In a further embodiment of the annular membrane wall 17 this can also be constructed in such a way that just before their connection to the other two parts 16a, 16b of the membrane 10 the marginal regions of the thinner annular membrane wall 17, having a cross-section of small radius, are curve-shaped and face the diagonal wall 11, as clearly shown by the reference numeral 21. The annular wall 17 then merges with the actual bead-shape which curves in the opposite direction.

The crater-like sealing ring 13 has a diameter which is only slightly larger than the flow passage 18 of the membrane 10. The crater-like sealing ring 13 furthermore has a triangular cross-section, its pointedly converging exposed end forms the sealing point 13a.

The operation of the nonreturn valve described is now described with the aid of such a nonreturn valve integrated in a device for medical parallel infusion. An infusion system (not shown) operating by gravity is connected to the inlet channel 6 and a further drug supply is administered via a pressure infusion system (also not shown) which is connected to the outlet channel 7 as a secondary connection.

The liquid column of the gravity-fed infusion system through the drillings 12 thus rests on the membrane 10 with the effect that its sealing part 16b, which is prestressed in the direction of the crater-like sealing ring 13, lifts off from the crater-like sealing ring 13. The infusion liquid via the drilling 18 in the sealing part 16b thus reaches further into the chamber 9 and then into the outlet channel 7. This situation also remains when the drug supply from the pressure infusion system takes place without an increase in pressure in the infusion catheter leading to the patient. However, if an increase in pressure takes place in the pressure infusion system, this also causes an increase in pressure in the catheter which retroacts on the chamber 9 and there acts on the entire rear surface of the membrane 10. Because of this initial tension the membrane ensures a quick and safe sealing of the nonreturn valve, thus ensuring that unintended drugs do not enter the gravity-fed infusion system.

A further increase in pressure causes the membrane 10 to become deformed to such an extent that the thin, profiled bead-like annular wall 17 comes to rest against the annular surface 15 of the diagonal wall 11, so that the annular wall is relieved of traction forces when under high pressure, thus preventing the destruction of the membrane. The said pressure increase in the catheter leading to the patient can be used for producing a signal which can alert the staff to the interruption in the operating condition.

The nonreturn valve described is preferably used in the field of medicine. However, it can also be used in pumps in other areas where the operating conditions are the same or similar.

I claim:

1. A nonreturn valve, in particular for use in connection with medical infusion appliances, comprising a housing with a central chamber into which open an inlet channel and an outlet channel, the channels being separated by a sealing membrane provided with a flow passage, wherein the membrane has a marginal part clamped in the housing, a central sealing part having a sealing surface, and a thinner annular wall that links both parts, wherein an inner wall side of the chamber (9) facing the outlet channel (7) comprises a sealing system for the membrane, the sealing system comprising a central crater-like ring having an annular sealing edge, wherein inflow from the inlet channel (6) to the membrane (10) takes place outside the crater-like sealing ring, and the flow passage (18) of the membrane (10) is located as an aperture within the crater-like sealing ring, wherein the thinner annular wall (17) of the membrane (10) generates a sealing prestress between the annular sealing edge and the sealing surface, and junctures (17a, 17b) adjacent to the marginal part (16a) and to the central sealing part (16b) of the membrane, the junctures being substantially coplanar with the sealing surface of the central sealing part (16b) and the annular sealing edge of the crater-like sealing ring.

2. Nonreturn valve according to claim 1, characterised in that a diagonal wall (11) with through-drillings (12) is provided in the inlet channel (6) on the outflow side before the membrane (10) and that the diagonal wall (11) has a recessed annular surface (15) as a stress-relieving support surface for the thinner annular wall (17) of the membrane (10) when under load.

3. Nonreturn valve according to claim 2, characterized in that the annular wall (17) has a symmetrically shaped cross-section, bead-shaped and whose apex points away from the inlet channel (6).

4. A nonreturn valve according to claim 2, wherein marginal regions (21) of the annular wall (17) comprise a generally curve shaped cross-section of small radius facing the inlet channel (6), the marginal regions of the annular wall (17) being connected to the membrane (10).

5. Nonreturn valve according to claim 2, characterized in that the crater-like sealing ring (13) has a diameter which is only slightly larger than the flow passage (18) of the membrane (10).

6. Nonreturn valve according to claim 1, characterised in that the annular wall (17) has a symmetrically shaped cross-section, bead-shaped and whose apex points away from the inlet channel (6).

7. A nonreturn valve according to claim 6, wherein marginal regions (21) of the annular wall (17) comprise a generally curve shaped cross-section of small radius facing the inlet channel (6), the marginal regions of the annular wall (17) being connected to the membrane (10).

8. Nonreturn valve according to claim 6, characterized in that the crater-like sealing ring (13) has a diameter which is only slightly larger than the flow passage (18) of the membrane (10).

9. A nonreturn valve according to claim 1, wherein marginal regions (21) of the annular wall (17) comprise a generally curve shaped cross-section of small radius facing the inlet channel (6), the marginal regions of the annular wall (17) being connected to the membrane (10).

10. Nonreturn valve according to claim 9, characterized in that the crater-like sealing ring (13) has a diameter which is only slightly larger than the flow passage (18) of the membrane (10).

11. Nonreturn valve according to claim 1, characterised in that the crater-like sealing ring (13) has a diameter which is only slightly larger than the flow passage (18) of the membrane (10).

12. Nonreturn valve according to claim 11, characterised in that the crater-like sealing ring (13) has a triangularly shaped cross-section, its exposed end, which tapers to a point, thereby forming a sealing point (13a).

* * * * *